United States Patent [19]

Hopp et al.

[11] 4,455,295

[45] Jun. 19, 1984

[54] N-(P-SULFOPHENYL) CINNAMAMIDE AS SUNSCREEN AGENT

[75] Inventors: Rudolf Hopp; Horst Finkelmeier, both of Holzminden; Roland Langner, Bevern, all of Fed. Rep. of Germany

[73] Assignee: Haarmann & Reimer GmbH, Holzminden, Fed. Rep. of Germany

[21] Appl. No.: 492,076

[22] Filed: May 6, 1983

[30] Foreign Application Priority Data

May 25, 1982 [DE] Fed. Rep. of Germany ....... 3219643

[51] Int. Cl.$^3$ ...................... A61K 7/44; C07C 143/53
[52] U.S. Cl. ................................ 424/60; 260/507 R; 260/501.21; 260/501.19; 260/501.15; 544/110; 548/579; 548/347; 548/184

[58] Field of Search ......... 424/60; 260/507 R, 501.19, 260/501.21, 501.15; 548/579, 184, 347, 215, 240; 544/110

[56] References Cited

FOREIGN PATENT DOCUMENTS 954911 12/1956 Fed. Rep. of Germany .
959052 2/1957 Fed. Rep. of Germany .

*Primary Examiner*—Nicky Chan
*Attorney, Agent, or Firm*—Sprung, Horn, Kramer & Woods

[57] ABSTRACT

N-(p-sulfophenyl)-cinnamamide, which is optionally present in the form of a salt, can be prepared by the reaction of cinnamoyl chloride with sulphanilic acid in the presence of a tertiary amine. The new compound can be used in light-protection agents.

7 Claims, No Drawings

N-(P-SULFOPHENYL) CINNAMAMIDE AS SUNSCREEN AGENT

The invention relates to the new N-(p-sulfophenyl)-cinnamamide and its salts, its preparation from cinnamoyl chloride and sulphanilic acid, and its use in light-protection agents.

The new compounds correspond to the formula

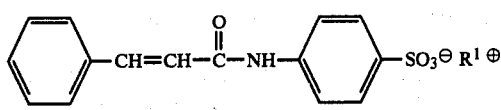
(I)

in which
$R^{1\oplus}$ represents a hydrogen ion, alkali metal ion or ammonium ion of the formula

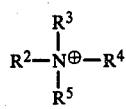

in which
$R^2$ to $R^5$ are identical or different and denote hydrogen, or lower alkyl which is optionally substituted by hydroxyl or aryl, it being possible for two lower alkyl groups to be optionally joined to form 5- membered or 6-membered ring which optionally contains an ether group.

It is of course also possible for N-(p-sulfophenyl)-cinnamamide or its salts to be present partially in non-ionic form or in another tautomeric form.

According to the invention, an alkali metal ion denotes in general a sodium, potassium or lithium ion, preferably a sodium ion.

According to the invention, lower alkyl denotes in general a straight-chain or branched hydrocarbon radical having 1 to about 6 carbon atoms. The methyl, ethyl, propyl, isopropyl, butyl, isobutyl, pentyl, isopentyl, hexyl and isohexyl radicals may be mentioned as examples. Preferred lower alkyl radicals are the methyl, ethyl, n-propyl and isopropyl radicals.

In the case in which the lower alkyl groups are joined to form 5-membered or 6-membered ring which optionally contains oxygen, a piperidine, pyrrolidine or morpholine ring is obtained, in accordance with the invention.

According to the invention, aryl denotes in general phenyl or tolyl.

The ammonium ions of the following amines may be mentioned as examples: triethylamine, N,N-dimethyl-benzyl-amine, morpholine, ethanolamine, 3-hydroxypropylamine, cyclohexylethanolamine, triethanolamine and the tetramethylammonium and tetraethylammonium ions.

Preferred new N-(p-sulfophenyl-cinnamamide correspond to the formula

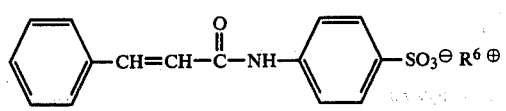
(II)

in which $R^{6\oplus}$ denotes a hydrogen or alkali metal ion or ethanolammonium, diethanolammonium or triethanol-ammonium.

The triethanolammonium salt and the sodium salt of N-(p-sulfophenyl)-cinnamamide are particularly preferred.

It is of course possible for N(p-sulfophenyl)-cinnamamide to be substituted by customary radicals. In particular, lower alkyl ($C_1$ to $C_6$), preferably methyl, or lower alkoxy ($C_1$ to $C_6$), preferably methoxy, may be mentioned in this context.

The new N-(p-sulfophenyl)-cinnamamide or one of its salts can be prepared by a process in which cinnamoyl chloride is reacted with sulphanilic acid in the presence of a tertiary amine, and if appropriate the N-(p-sulfophenyl)-cinnamamide obtained is converted into the corresponding salt by reaction with an alkali metal hydroxide, an amine of the general formula

(III)

or an ammonium hydroxide of the formula

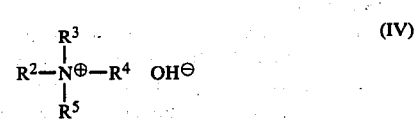
(IV)

in which
$R^2$ to $R^5$ have the abovementioned meaning.

The reaction of the cinnamoyl chloride with sulphanilic acid is carried out according to the invention in general in a polar solvent, such as acetonitrile, butyronitrile or acetone.

The process according to the invention is carried out in general in the temperature range from 50° C. to the boiling point of the solvent. The process according to the invention is preferably carried out in the boiling range of the particular solvent. The boiling range of the solvent can of course be changed by increasing the pressure. Thus, it can be advantageous to carry out the process according to the invention at a temperature of up to about 150° C., after an appropriate increase in the pressure.

The process according to the invention is carried out as a rule in the presence of an organic base, preferably a tertiary amine. Tertiary amines which may be mentioned are amines which are substituted by lower alkyl ($C_1$ to about $C_6$), phenyl or benzyl. Pyridine, tri-n-butylamine or N,N-dimethylbenzylamine may be mentioned as examples.

In general, the tertiary amine is added in an amount which is sufficient to neutralize the sulphanilic acid and to bind the hydrogen chloride liberated during the reaction.

The preparation of the salts of N-(p-sulfophenyl)-cinnamamide is advantageously carried out by combining equimolar amounts of the components. The neutralization point may be additionally monitored by pH measurements.

The new N-(p-sulfophenyl)-cinnamamide and its salts can be advantageously used as active compounds in light-protection agents which have a high water content.

The ultraviolet rays of the sun which have wavelengths of 290–320 nm produce photo-erythema ("sunburn") on contact with the skin. There is therefore a need for light-protection agents for the skin which have a good protective action in the wavelength range mentioned, but are also excellently tolerated by the skin, have excellent stability to light, heat and moisture, and may be readily incorporated in the cosmetic bases customary for light-protection agents. Since a large number of these bases contain water, it is advantageous if the active compound is water-soluble.

Thus, for example, the commercially available 2-phenyl-benzimidazole-5-sulphonic acid is itself insoluble in water, and can be employed, in the form of salts, only in the pH range from 6.0 to 8.5 in the sunscreen formulation (tradename "Eusolex ®" from Merck, Darmstadt, order number 16/62/3/177).

The consequence of this is that it is precipitated under acidic conditions occurring during use, and cannot be applied onto the skin without problems.

In contrast, the new active compounds are stable under all conditions of use, and are not precipitated from water-containing solutions. They are sufficiently soluble in the pH range from 3 to 12 for use in light-protection agents.

The N-(p-sulfophenyl)-cinnamamide according to the invention, and the corresponding salts, afford particularly good absorption of the erythema-producing ultraviolet rays of the sun in the range of 290–320 nm. They are stable to light, heat and moisture, are almost colorless and odorless and can be particularly advantageously used in sunscreen agents. The invention therefore also relates to sunscreen agents which contain N-(p-sulfophenyl)-cinnamamide or the corresponding salts.

The sunscreen agents according to the invention can be prepared by incorporating the N-(p-sulfophenyl)-cinnamamide or its salts into a cosmetic base customary for sunscreen agents. Incorporation is effected by customary methods of distribution, such as, for example, stirring in or homogenization.

Owing to the very good water-solubility of the compounds according to the invention, they are particularly suitable for incorporation into aqueous and aqueous/alcoholic solutions or phases of cosmetic bases. Examples of customary cosmetic bases are creams, lotions, ointments, solutions, sprays, milks and gels (G. H. Nowak, "Die kosmetischen Präparate" (Cosmetic Formulations), 2nd edition, 1975).

Creams for the light-protection agents according to the invention are emulsions of the water-in-oil and oil-in-water types.

Lotions for the light-protection agents according to the invention are alcoholic/aqueous oil/alcohol mixtures.

Ointments for the light-protection agents according to the invention are pharmaceutical creams.

The solutions for the light-protection agents according to the invention are, for example, solutions of the light-protection agent in cosmetic solvents, such as oils and alcohols.

Sprays for the light-protection agents according to the invention are solutions in conjunction with a propellant.

Milks for the light-protection agents according to the invention are liquid, stable emulsions of the water-in-oil and oil-in-water types.

The constituents of the cosmetic bases are customary ones and are in themselves known. It is also possible to add perfume oils.

Depending on the cosmetic base, the content of N-(p-sulfophenyl)-cinnamamide according to the invention, or of one of its salts, in the light-protection agents is 1 to 6%, preferably 2 to 5%, relative to the total amount of the cosmetic base.

It is of course also possible for the light-protection agents according to the invention to contain mixtures of N-(p-sulfophenyl)-cinnamamide and the corresponding salts.

It is of course also possible in addition to add other active compounds for light protection, for example oil-soluble active compounds, such as 2-ethyl-hexyl p-methoxycinnamate or isoamyl p-methoxycinnamate. However, this is in general not necessary for adequate protection from the sun.

EXAMPLE 1

To a suspension of 86.5 g of anhydrous sulphanilic acid in 120 g of acetone are added dropwise, while stirring at 30° C., 168.8 g of N,N-dimethyl-benzylamine in the course of 15 minutes, followed by a solution of 83.5 g of cinnamoyl chloride in 80 g of acetone in the course of 50 minutes. After the addition is complete, the reaction temperature is increased to the reflux temperature for 1 hour, and the acetone is then removed as completely as possible. The residue which remains is stirred for 1 hour at 80° C., 90 g of 50% strength sodium hydroxide solution in 500 ml of water are then added, and the mixture is again heated to 80° C. and left to stand at this temperature for 15 minutes. The phases are separated and the aqueous phase is washed with 50 g of toluene. The aqueous phase, which is still hot, is diluted with 800 ml of water and neutralized with concentrated sulphuric acid. The cooled aqueous solution is then added dropwise in the course of 20 minutes to 1 kg of 50% strength sulphuric acid, while stirring vigorously. The precipitated crystals are separated off and dissolved in 4 liters of water, the solution is filtered, and again brought to crystallization by the addition of 100 g of concentrated sulphuric acid. 111 g of pure N-(p-sulfophenyl)-cinnamamide (corresponding to 75.9% of theory) with a melting point of 235°–237° C. are obtained. UV spectrum (in methanol):

$\lambda_{max} = 300$ nm, E (1%, 1 cm) = 960

Neutralization of an aqueous solution with the equimolecular amount of base gives the corresponding salts after the water has been removed by being distilled off:

| Base | Melting point (°C.) | UV spectra (nm) $\lambda_{max}$ (nm) | E (1%, 1 cm) |
|---|---|---|---|
| NaOH | >300 | 299/301 | 1,010 |
| KOH | >300 | 301 | 930 |
| NH3 | 293->300 | 300 | 1,036 |
| Methylamine | 266–271 | — | |
| Piperidine | 214–224 | — | |
| Pyrrolidine | 219–227 | — | |
| Morpholine | 190–202 | — | |
| Triethylamine | 180–197 | 300 | 830 |
| Ethanolamine | 274 | 303 | 950 |
| 3-Hydroxypropylamine | 207–216 | — | |
| Cyclohexylethanolamine | 186–188 | 300 | 772 |
| Triethanolamine | 169–170 | 300 | 765 |
| Tetramethylammonium | >300 | — | |

-continued

| Base | Melting point (°C.) | UV spectra (nm) $\lambda_{max}$ (nm) | E (1%, 1 cm) |
|---|---|---|---|
| hydroxide | | | |

EXAMPLE 2

Sunscreen milk o/w (oil-in-water)

| | | Parts by weight |
|---|---|---|
| (A) | Cetylstearyl alcohol with approx. 12 mols of ethylene oxide | 1.00 |
| | Cetylstearyl alcohol with approx. 20 mols of ethylene oxide | 4.50 |
| | Cetyl-stearyl alcohol | 2.50 |
| | Mixture of mono-diglycerides, fatty alcohols, triglycerides and wax esters | 5.00 |
| | 2-Octyl-dodecanol | 3.00 |
| | Isopropyl myristate | 5.00 |
| | Decyl oleate | 3.00 |
| | Propyl p-hydroxybenzoate | 0.08 |
| (B) | Distilled water | 27.82 |
| | Methyl p-hydroxybenzoate | 0.20 |
| | Imidazolidinylurea derivative | 0.20 |
| | N—(p-sulfophenyl)-cinnamamide as the triethanolamine salt (33.2% of salt in water) | 10.00 |
| (C) | Distilled water | 35.00 |
| | Carboxyvinyl polymer | 0.40 |
| | Sodium hydroxide solution (10% strength) | 1.60 |
| (D) | Perfume oil | 0.70 |

The components (A) are combined, and heated to 75° C. The components (B) are dissolved at 85° C. and stirred into (A). The carboxyvinyl polymer from part (C) is dispersed in the water constituent and the solution neutralized with sodium hydroxide solution. The gel formed is stirred into the emulsion comprising (A) and (B), at 55° C. The emulsion is then coooled to 35-40 C., (D) is added, and the mixture is cooled to room temperature while stirring.

EXAMPLE 3

Sunscreen milk o/w (oil-in-water)

| | | Parts by weight |
|---|---|---|
| (A) | Polyoxyethylene stearyl ether | 4.00 |
| | Mixture of glycerol mono- and di-stearate with non-ionic surfactants | 2.50 |
| | Mixture of mono-diglycerides, fatty alcohols, triglycerides and wax esters | 4.00 |
| | Cetyl alcohol and stearyl alcohol | 2.00 |
| | 2-Ethylhexyl p-methoxycinnamate | 4.00 |
| | Isopropyl myristate | 2.00 |
| | Paraffin oil | 1.50 |
| | Propyl p-hydroxybenzoate | 0.08 |
| (B) | Distilled water | 29.82 |
| | Methyl p-hydroxybenzoate | 0.20 |
| | Imidazolidinylurea derivative | 0.20 |
| | N—(p-sulfophenyl)-cinnamamide as the triethanolamine salt (33,2% of salt in water) | 12.00 |
| (C) | Distilled water | 35.00 |
| | Carboxyvinyl polymer | 0.40 |
| | Sodium hydroxide solution (10% strength) | 1.60 |
| (D) | Perfume oil | 0.70 |

The preparation is carried out analogously to Example 2.

EXAMPLE 4

Light-protection gel (aqueous)

| | | Parts by weight |
|---|---|---|
| (A) | Distilled water | 71.25 |
| | Allantoin | 0.10 |
| | Polyethylene glycol MW 400 | 5.00 |
| | Imidazolidinylurea derivative | 0.20 |
| | Methylchloroisothiazolinones + methylisothiazolinones | 0.03 |
| (B) | Carboxyvinyl polymer | 0.80 |
| | Triethanolamine | 1.12 |
| (C) | N—(sulfophenyl)-cinnamamide as the triethanolamine salt (33.2% of salt in water) | 20.00 |
| (D) | Perfume oil | 0.30 |
| | 2-Hydroxy-fatty alcohol alkoxylate | 1.20 |

The components (A) are dissolved, the carboxyvinyl polymer from (B) is dispersed in the solution and the dispersion is neutralized with triethanolamine. (C) is then stirred into the gel comprising (A) and (B) and, finally, the components from (D) are mixed, and the mixture is stirred into the gel.

EXAMPLE 5

Light-protection gel (aqueous/alcoholic)

| | | Parts by weight |
|---|---|---|
| (A) | Ethyl alcohol 96 vol. % | 25.00 |
| | Distilled water | 50.25 |
| | Allantoin | 0.10 |
| | Polyethylene glycol MW 400 | 5.00 |
| | Imidazolidinylurea derivative | 0.20 |
| | Methylchloroisothiazolinones + methylisothiazolinones | 0.03 |
| (B) | Carboxyvinyl polymer | 0.80 |
| | Triethanolamine | 1.12 |
| (C) | N—(p-sulfophenyl)-cinnamamide as the triethanolamine salt (33.2% of salt in water) | 16.00 |
| (D) | Perfume oil | 0.30 |
| | Hydrogenated ethoxylated castor oil | 1.20 |

The preparation is carried out analogously to Example 4.

EXAMPLE 6

Sunscreen cream o/w (oil-in-water)

| | | Parts by weight | Parts by weight |
|---|---|---|---|
| (A) | Mixture of mono- and diglycerides of palmitic and stearic acid with polyethylene glycol-(40)-stearate | 7.00 | 7.00 |
| | Cetyl-stearyl alcohol | 2.00 | 2.00 |
| | Glycerol mono-distearate | 4.00 | 4.00 |
| | Isoamyl p-methoxy-cinnamate | — | 4.00 |
| | 2-Octyl-dodecanol | 4.00 | — |
| | Decyl oleate | 4.00 | 4.00 |
| | Isopropyl myristate | 5.00 | 5.00 |
| | Paraffin oil | 1.00 | 1.00 |
| | Propyl p-hydroxybenzoate | 0.08 | 0.08 |
| (B) | Distilled water | 24.82 | 24.82 |
| | Methyl p-hydroxybenzoate | 0.20 | 0.20 |
| | Imidazolidinylurea derivative | 0.20 | 0.20 |
| | N—(p-sulfophenyl)-cinnamamide as the triethanolamine salt (33.2% of salt in water) | 20.00 | 20.00 |
| (C) | Distilled water | 25.00 | 25.00 |
| | Carboxyvinyl polymer | 0.40 | 0.40 |

| | Parts by weight | Parts by weight |
|---|---|---|
| Sodium hydroxide solution (10% strength) | 1.60 | 1.60 |
| (D) Perfume oil | 0.70 | 0.70 |

The preparation is carried out analogously to Example 2.

It is understood that the specification and examples are illustrative but not limitative of the present invention and that other embodiments within the spirit and scope of the invention will suggest themselves to those skilled in the art.

We claim:

1. N-(p-sulfophenyl)-cinnamamide or a salt thereof of the formula

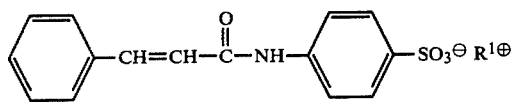

in which
R$^{1\oplus}$ is a hydrogen ion, alkali metal ion or ammonium ion of the formula

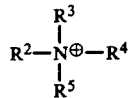

, and
R$^2$ to R$^5$ each independently is hydrogen, or lower alkyl which is optionally substituted by hydroxyl or aryl, or two of them are joined to form a 5-membered or 6-membered ring which optionally contains an oxygen atom.

2. A compound or salt according to claim 1, wherein R$^{1\oplus}$ is a hydrogen ion, alkali metal or mono-, di- or triethanolammonium ion.

3. A salt according to claim 1, wherein R$^{1\oplus}$ is a sodium or triethanolammonium ion.

4. In a sunscreen composition comprising a sunscreen base and a sunscreening agent, the improvement which comprises employing as said agent a compound or salt according to claim 1.

5. A composition according to claim 4, wherein the agent is present in about 1 to 6% by weight.

6. In a sunscreen composition comprising a sunscreen base and a sunscreening agent, the improvement which comprises employing as said agent a compound or salt according to claim 2 in about 2 to 5%.

7. A sunscreen composition according to claim 6, wherein R$^{1\oplus}$ is a sodium or triethanolammonium ion.

* * * * *